US008693852B2

(12) United States Patent  
Baraky

(10) Patent No.: US 8,693,852 B2  
(45) Date of Patent: Apr. 8, 2014

(54) WARMERS FOR SCENTED OILS

(75) Inventor: David John Baraky, Duxbury, MA (US)

(73) Assignee: PartyLite Worldwide, Inc., Plymouth, MA (US)

( * ) Notice: Subject to any disclaimer, the term of this patent is extended or adjusted under 35 U.S.C. 154(b) by 910 days.

(21) Appl. No.: 12/782,811

(22) Filed: May 19, 2010

(65) Prior Publication Data  
US 2011/0286726 A1 Nov. 24, 2011

(51) Int. Cl.  
A01M 13/00 (2006.01)

(52) U.S. Cl.  
USPC ............ 392/386; 392/390; 392/391; 392/393

(58) Field of Classification Search  
None  
See application file for complete search history.

(56) References Cited

U.S. PATENT DOCUMENTS

| | | | | |
|---|---|---|---|---|
| 1,403,548 A | * | 1/1922 | Gudeman | 422/125 |
| 1,535,486 A | | 4/1925 | Lundy | |
| 1,547,160 A | | 7/1925 | Bailey | |
| 1,556,680 A | * | 10/1925 | Dorment | 422/125 |
| 1,565,500 A | * | 12/1925 | Ritter | 392/393 |
| 1,732,707 A | * | 10/1929 | Winsboro | 422/125 |
| 1,960,098 A | | 5/1934 | Breitenbach | |
| 1,992,684 A | | 2/1935 | Weinberger | |
| 2,293,235 A | | 8/1942 | Zahner | |
| 2,435,756 A | * | 2/1948 | Schlesinger | 422/305 |
| 2,557,502 A | | 6/1951 | Fusay et al. | |
| 2,742,342 A | | 4/1956 | Dew et al. | |
| 2,757,278 A | | 7/1956 | Cloud | |
| 2,775,006 A | | 12/1956 | Kranc | |
| 2,824,208 A | | 2/1958 | Bauer | |
| 3,443,083 A | * | 5/1969 | Curran | 362/643 |
| 3,890,085 A | | 6/1975 | Andeweg | |
| 3,959,642 A | | 5/1976 | Turro | |
| 4,074,111 A | * | 2/1978 | Hunter | 392/393 |
| 4,493,011 A | * | 1/1985 | Spector | 362/96 |
| 4,579,717 A | * | 4/1986 | Gyulay | 422/125 |
| D288,842 S | | 3/1987 | Kwiatkowski | |
| 4,647,428 A | * | 3/1987 | Gyulay | 422/4 |
| 4,781,895 A | * | 11/1988 | Spector | 422/125 |
| 4,892,711 A | * | 1/1990 | Tendick, Sr. | 422/125 |
| 4,965,490 A | * | 10/1990 | Ratner | 313/569 |
| 5,647,052 A | * | 7/1997 | Patel et al. | 392/390 |

(Continued)

FOREIGN PATENT DOCUMENTS

| | | |
|---|---|---|
| GB | 2326342 A | 12/1998 |
| WO | 00/37848 | 6/2000 |

OTHER PUBLICATIONS

European Search Report dated Sep. 26, 2011 from EP 11166569.1.

Primary Examiner — Thor Campbell  
(74) Attorney, Agent, or Firm — Ohlandt, Greeley, Ruggiero & Perle, L.L.P.

(57) ABSTRACT

A warmer for scented oil is provided. The warmer includes a base, a cover removably positioned on the base, and a warming device. The cover has a substantially spherical shape with an opening at an upper apex and an open channel formed in the cover at the upper apex around an outer periphery of the opening. The open channel is configured to receive the scented oil. The warming device is in a heat conductive relationship with the cover so that scented oil in the open channel is warmed by the warming device. The warming device can be one or more of a lighting device with an incandescent light bulb, a resistance heater with or without a lighting device such as a light emitting diode, or a candle.

18 Claims, 7 Drawing Sheets

(56) References Cited

U.S. PATENT DOCUMENTS

| | | | |
|---|---|---|---|
| 5,651,942 A * | 7/1997 | Christensen | 422/125 |
| D392,032 S | 3/1998 | Zaragoza et al. | |
| 5,891,400 A * | 4/1999 | Ansari et al. | 422/125 |
| 6,035,098 A * | 3/2000 | Chipalkatti et al. | 392/393 |
| 6,106,786 A | 8/2000 | Akahoshi | |
| 6,328,935 B1 * | 12/2001 | Buccellato | 422/125 |
| 6,349,168 B1 * | 2/2002 | Jaworski | 392/392 |
| D454,190 S | 3/2002 | Trocola | |
| 6,354,710 B1 | 3/2002 | Nacouzi | |
| 6,371,453 B1 | 4/2002 | Hunter | |
| 6,381,408 B1 * | 4/2002 | Jaworski et al. | 392/392 |
| 6,413,476 B1 * | 7/2002 | Barnhart | 422/124 |
| 6,419,122 B1 | 7/2002 | Chown | |
| 6,482,365 B1 * | 11/2002 | Soller | 422/126 |
| D475,445 S | 6/2003 | Kumar | |
| 6,638,060 B1 | 10/2003 | Rivard et al. | |
| D509,893 S | 9/2005 | Sevy | |
| 6,966,665 B2 * | 11/2005 | Limburg et al. | 362/96 |
| 7,067,772 B2 | 6/2006 | Tanner et al. | |
| 7,083,162 B2 * | 8/2006 | He et al. | 261/142 |
| 7,132,084 B1 | 11/2006 | Roumpos | |
| 7,133,605 B2 * | 11/2006 | Niemeyer | 392/390 |
| 7,195,739 B1 | 3/2007 | Penman et al. | |
| D544,084 S | 6/2007 | Michael et al. | |
| 7,329,839 B2 | 2/2008 | Palmer | |
| 7,503,668 B2 * | 3/2009 | Porchia et al. | 362/161 |
| D597,645 S | 8/2009 | Thompson | |
| 7,604,378 B2 * | 10/2009 | Wolf et al. | 362/253 |
| 7,625,578 B2 * | 12/2009 | Davis et al. | 424/409 |
| D611,587 S | 3/2010 | Dineen | |
| D614,277 S | 4/2010 | Hsiao | |
| 7,824,627 B2 * | 11/2010 | Michaels et al. | 422/128 |
| 7,997,772 B2 * | 8/2011 | Avtzon et al. | 362/392 |
| 8,364,028 B1 * | 1/2013 | Vaske et al. | 392/390 |
| 8,385,730 B2 * | 2/2013 | Bushman et al. | 392/386 |
| 2003/0007887 A1 * | 1/2003 | Roumpos et al. | 422/1 |
| 2005/0016985 A1 * | 1/2005 | Haas et al. | 219/438 |
| 2005/0030747 A1 | 2/2005 | Bogdal | |
| 2006/0018786 A1 | 1/2006 | Tolman et al. | |
| 2006/0163240 A1 | 7/2006 | Xiao | |
| 2006/0239870 A1 * | 10/2006 | Schutte et al. | 422/125 |
| 2006/0269885 A1 | 11/2006 | Kennington | |
| 2007/0047931 A1 * | 3/2007 | Niemeyer | 392/390 |
| 2009/0291400 A1 | 11/2009 | Levy | |
| 2012/0020052 A1 * | 1/2012 | McCavit et al. | 362/96 |
| 2012/0318780 A1 * | 12/2012 | Juarez | 219/209 |

* cited by examiner

US 8,693,852 B2

WARMERS FOR SCENTED OILS

BACKGROUND OF THE INVENTION

1. Field of the Invention

The present disclosure is related to warmers for scented oils.

2. Description of Related Art

The release of scents to cover or mask unpleasant aromas and/or to provide a desired aroma have been practiced for many years. The heating of scented oils is one known method of releasing scents.

However, it is has been determined by the present disclosure that there is a need for warmers for scented oils that overcome, alleviate, and/or mitigate one or more deleterious effects of prior art warmers.

SUMMARY OF THE INVENTION

A warmer for scented oil is provided. The warmer includes an enclosure that surrounds a warming device. The enclosure may include a single component or multiple components, which fit together to form an enclosure around the warming device. The enclosure has an opening at an upper apex, with an open channel formed at the upper apex around the outer periphery of the opening. The open channel is configured to receive the scented oil. The warming device is in a heat conductive relationship with the enclosure so that scented oil in the open channel is warmed by the warming device.

In some embodiments, the open channel includes an inner upstanding rim around the outer periphery of the opening and an outer upstanding rim spaced from the inner rim.

The warming device can be, in some embodiments, a lighting device with an incandescent light bulb. The lighting device can be secured to a base of the enclosure so that the enclosure shields substantially all of the incandescent light bulb. Here, the enclosure can include a decorative pattern defined on an external surface and/or one or more portions of the enclosure can be at least partially translucent.

The warming device can also be, in other embodiments, a resistance heater. The resistance heater can be secured to a base of the enclosure. In these embodiments, the warmer can optionally include a lighting device such as, but not limited to, a light emitting diode. Again, the enclosure can include a decorative pattern defined on an external surface and/or one or more portions of the enclosure can be at least partially translucent.

The warming device in still other embodiments can be a candle that is removably positionable within the enclosure so that the enclosure shields substantially all of the candle with the candle being at a center of the opening. The warmer can optionally include at least one vent opening defined in the enclosure. The vent opening can be, for example, a plurality of evenly spaced openings defined near a base of the enclosure. Also, the enclosure can include a decorative pattern defined on an external surface and/or one or more portions of the enclosure can be at least partially translucent.

A warmer for scented oil having a base, a cover, a vent opening defined between the cover and the base, and a candle is also provided. The cover has an opening at an upper apex and is removably positioned on the base. An open channel is formed in the cover around an outer periphery of the opening, with the open channel being configured to receive the scented oil therein. The candle is removably positionable on the base with the candle being at a center of the opening. In this manner, the cover is in a heat conductive relationship with the candle so that scented oil in the open channel is warmed by the candle. In various embodiments, the cover can include a decorative pattern defined on an external surface and/or the cover can be at least partially translucent.

The above-described and other features and advantages of the present disclosure will be appreciated and understood by those skilled in the art from the following detailed description, drawings, and appended claims.

DETAILED DESCRIPTION OF THE INVENTION

Figure 1:
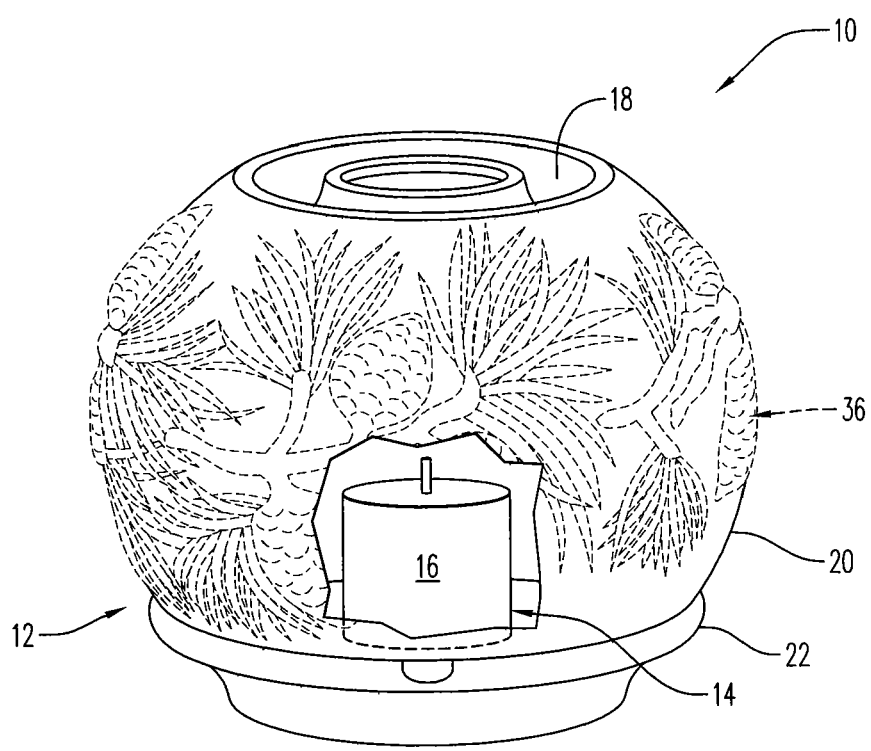
FIG. 1 is a front perspective view of a warmer for scented oil according to an exemplary embodiment of the present disclosure.
Figure 2:
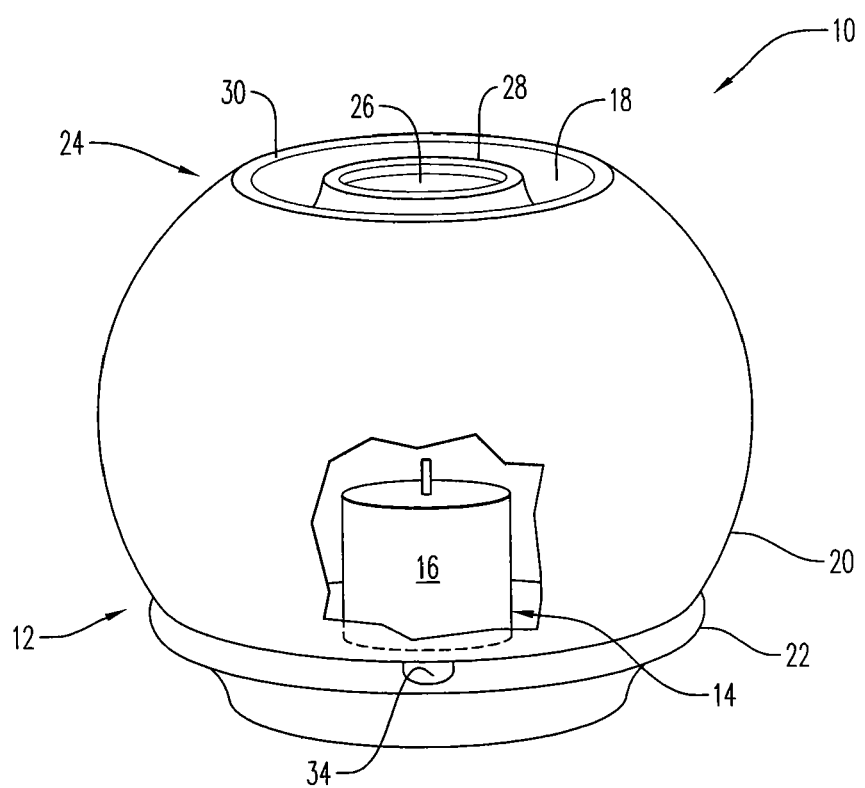
FIG. 2 is a front perspective view of the warmer of FIG. 1 having portions of the cover cut away to show a first embodiment of a warming device.
Figure 3:
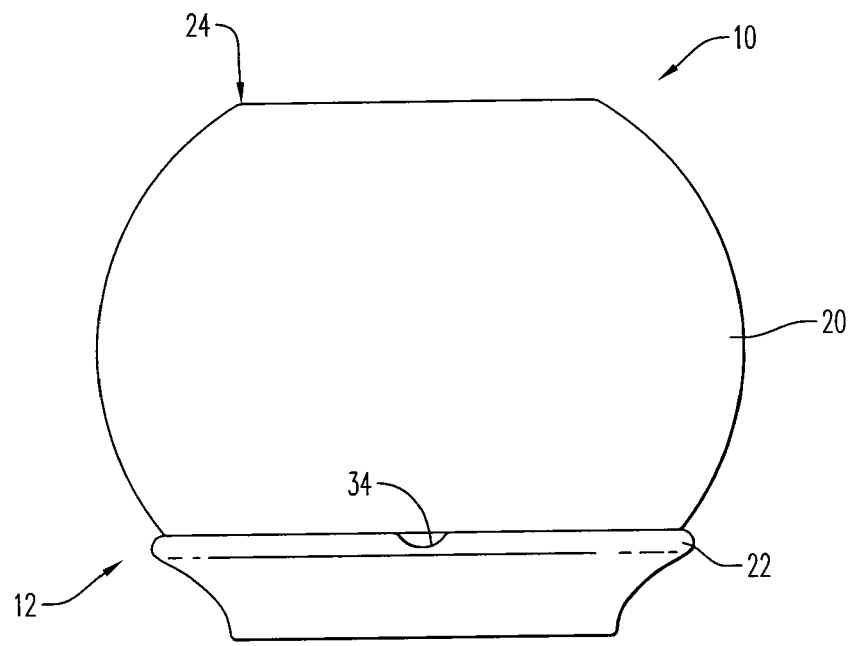
FIG. 3 is a first side view of the warmer of FIG. 1.
Figure 4:
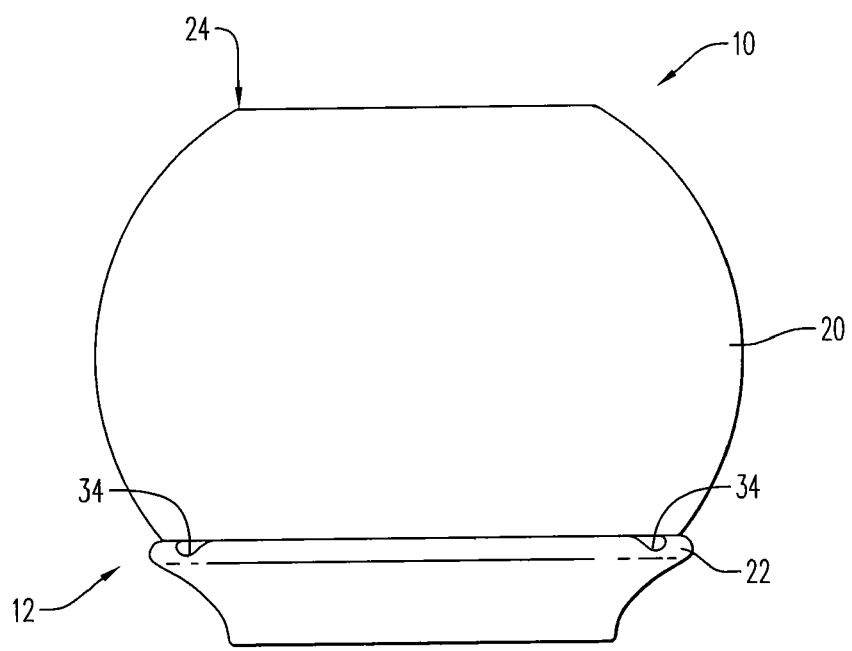
FIG. 4 is a second side view of the warmer of FIG. 1, which is offset from the first side view of FIG. 3 by one hundred and eighty degrees.
Figure 5:
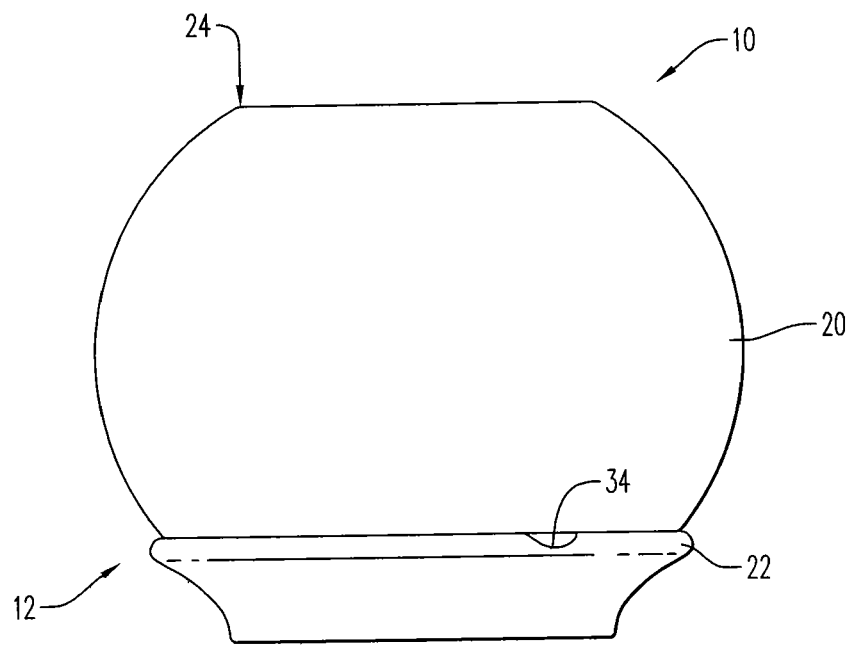
FIG. 5 is a third side view of the warmer of FIG. 1, which is offset from the first side view of FIG. 3 by one ninety degrees.
Figure 6:
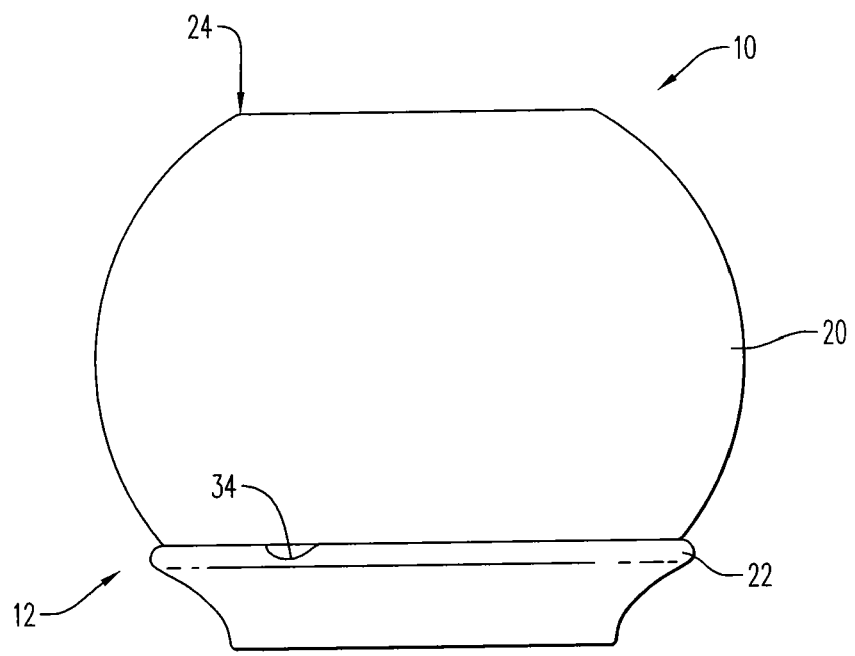
FIG. 6 is a fourth side view of the warmer of FIG. 1, which is offset from the first side view of FIG. 3 by two hundred seventy degrees.
Figure 7:
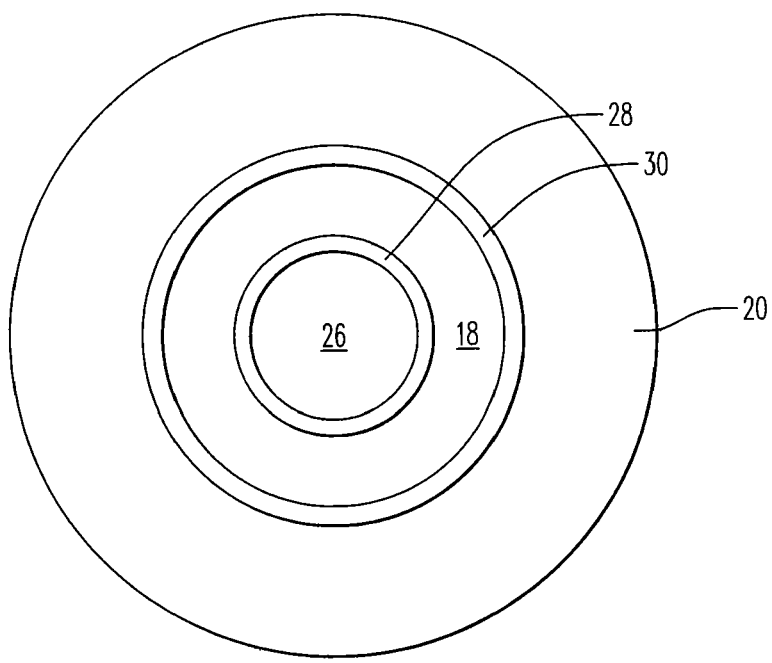
FIG. 7 is a top view of the warmer of FIG. 1.
Figure 8:
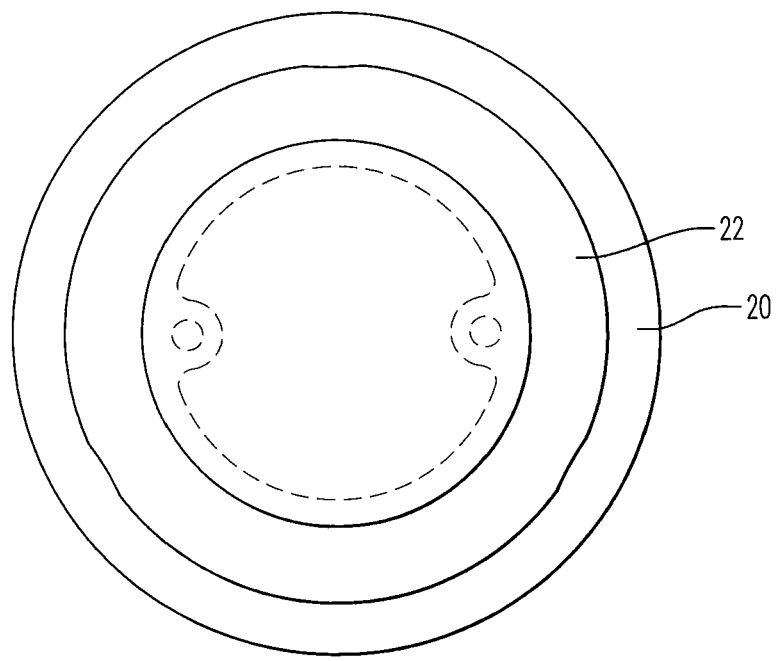
FIG. 8 is a bottom view of the warmer of FIG. 1.

Referring to the drawings and in particular to FIGS. 1 through 8, an exemplary embodiment of a warmer for scented oils is shown and is generally referred to by reference numeral 10. Warmer 10 includes an enclosure 12 and a warming device 14. In the embodiment of FIG. 1, warming device 14 is illustrated by way of example as a candle 16, which is shown in phantom.

Advantageously, warmer 10 is configured to use the heat generated by warming device 14 to heat enclosure 12. Enclosure 12 conducts the heat received from warming device 14 to warm scented oil (not shown) within an open channel 18 defined in the enclosure, where the open channel is configured to receive scented oil therein.

As used herein, the term "scented oil" shall mean any composition, in a liquid form, a semi-solid form, or a solid form, that includes a scent within the composition, where the scent is released upon heating of the composition to a desired temperature at a known release rate.

In some embodiments, warmer 10 includes open channel 18 pre-filled with scented oil in a solid or semi-solid form. In other embodiments, warmer 10 includes an empty open channel 18, which can be filled at the time of use by the user.

In the illustrated embodiment, enclosure 12 includes two components, namely a cover 20 and a base 22. Of course, it is contemplated by the present disclosure for enclosure 12 to be a single unitary component or for the enclosure to include more than two components, which fit together to form the desired enclosure around the warming device.

Cover 20 includes an upper apex or surface 24 with an opening 26 defined therethrough. Open channel 18 is formed in cover 20 at upper apex 24 around an outer periphery of opening 26. Opening 26 allows light and heat generated by candle 16 to escape cover 20. In addition, cover 20 is in a heat conductive relationship with warming device 14 so that the scented oil in open channel 18 is warmed by the warming device.

Cover 20 removably positioned on base 22 so that the user can selectively access candle 16 as needed for lighting, extinguishing, and/or replacement of the candle.

Open channel 18 includes an inner upstanding rim 28 around the outer periphery of opening 26 and an outer upstanding rim 30 spaced from the inner rim. In this manner, scented oil within open channel 18 is retained by rims 28, 30 so that the scented oil does not flow down an outer surface 32 of cover or flow into the inner area of the cover through opening 26.

Candle 16 is removably positioned on base 22 so that cover 20 shields or encloses substantially all of the candle and so that the candle is at a center of opening 26. Surprisingly, it has been determined by the present disclosure that heat from candle 16 can be sufficiently conducted to cover 20 even though the cover is not positioned directly over the candle. In this manner, warmer 10 allows light from candle 16 to exit through the top of the cover, yet still provides sufficient heat to release the scent from the scented oil in open channel 18.

In some embodiments, warmer 10 can include one or more openings 34 defined between cover 20 and said base 22. Vent openings 34 can ensure that candle 16 has sufficient oxygen to remain lit, and provides a convective air current through warmer 10 from vent openings 34 towards opening 18.

In the illustrated embodiment, vent openings 34 are shown as three evenly spaced indentations defined in base 2. Of course, it is contemplated by the present disclosure for there to be any desired number of vent openings 34 and for the openings to be positioned in any desired manner. Further, it is contemplated by the present disclosure for vent openings 34 to be formed in cover 20, base 22, or any combinations thereof.

In other embodiments, cover 20 can include one or more decorative patterns 36 (only one shown) defined on external surface 32.

Also, it is contemplated by the present disclosure for cover 20 to be at least partially translucent to allow at least a portion of the light generated by candle 16 to escape the cover. As used herein, the term "translucent" shall mean that at least some portion of visible light can pass through the cover by way of openings in the cover and/or by way of the property of the materials from which the cover is made allowing light to pass therethrough.

Enclosure 12 can be formed of any material sufficient to conduct heat from warming device 14 to open channel 18 and provide, when desired, the aforementioned translucent property. In a preferred embodiment, enclosure 12 is formed of a material selected from the group consisting of glass, ceramic, and any combinations thereof.

In the illustrated embodiments, cover 20 is shown having a substantially spherical shape. Of course, it is contemplated by the present disclosure for cover 20 to have any desired shape.

It should also be recognized that warmer 10 is described above by way of example as using candle 16 as the warming device 14. Of course, it is contemplated by the present disclosure for warming device 14 to include any device configured to provide heat to enclosure 12 in sufficient amount so as to release the scent from the scented oil in open channel 18 of the enclosure.

Figure 9:
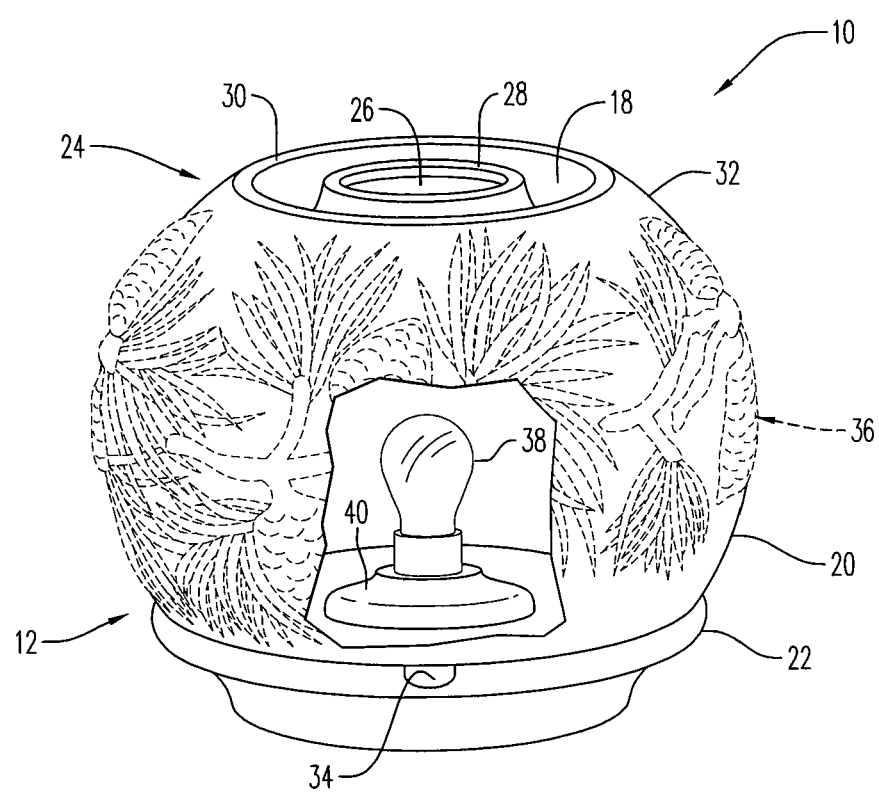
FIG. 9 is a front perspective view of the warmer of FIG. 1 having portions of the cover cut away to show a second embodiment of a warming device according to an exemplary embodiment of the present disclosure.

Referring now to FIG. 9, warmer 10 is illustrated using an incandescent light bulb 38 as warming device 16. Here, incandescent light bulb 36 is formed as part of a lighting device 40, which is secured to base 22. Cover 20 shields substantially all of incandescent light bulb 38. As discussed in detail above, cover 20 can include decorative pattern 36 defined on an external surface 32 thereof and/or the cover can be at least partially translucent. Lighting device 40 can be selectively placed in electrical communication with a power source (not shown) such as, but not limited to, a battery or an electrical outlet.

Figure 10:
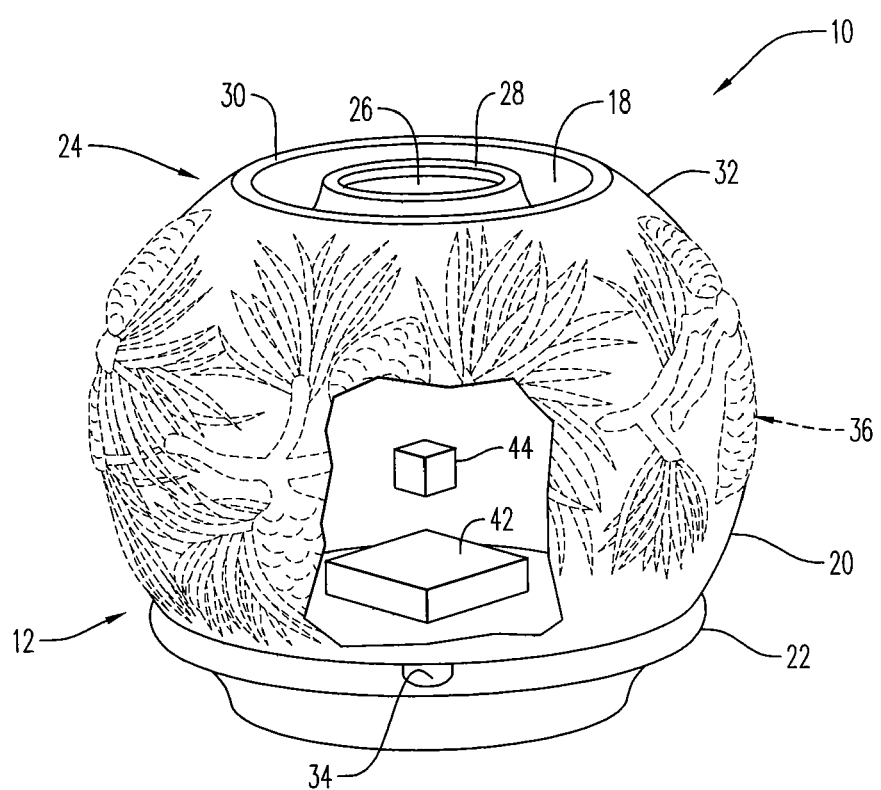
FIG. 10 is a front perspective view of the warmer of FIG. 1 having portions of the cover cut away to show a third embodiment of a warming device according to an exemplary embodiment of the present disclosure.

Referring now to FIG. 10, warmer 10 is illustrated using a resistance heater 42 as warming device 14. Here, resistance heater 42 can be secured to or formed as part of base 22. Also, warmer 10 can, in some embodiments, further include a lighting device 44 such as, but not limited to a light emitting diode (LED). Cover 20 shields substantially all of resistance heater 42 and, when present, lighting device 44. As discussed in detail above, cover 20 can include decorative pattern 36 defined on an external surface 32 thereof and/or the cover can be at least partially translucent. Resistance heater 42, and when present lighting device 44, can be selectively placed in electrical communication with a power source (not shown) such as, but not limited to, a battery or an electrical outlet.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

What is claimed is:

1. A warmer for scented oil, comprising:
    an enclosure having a base and a cover removably positioned on said base, said cover having an opening defined at an upper apex of said cover;
    an open channel formed in said cover at said upper apex around an outer periphery of said opening, said open channel being configured to receive the scented oil therein; and
    a warming device in heat conductive relationship with said enclosure so that scented oil in said open channel is warmed by said warming device, wherein said enclosure encloses substantially all of said warming device.

2. The warmer of claim 1, wherein said open channel comprises an inner upstanding rim around the outer periphery of said opening and an outer upstanding rim spaced from said inner rim.

3. The warmer of claim 1, wherein said warming device comprises a lighting device having an incandescent light bulb.

4. The warmer of claim 3, wherein said lighting device is in said enclosure so that said enclosure shields substantially all of said incandescent light bulb.

5. The warmer of claim 4, further comprising a decorative pattern defined on an external surface of said enclosure.

6. The warmer of claim 5, wherein said enclosure has a portion that is at least partially translucent.

7. The warmer of claim 1, wherein said warming device comprises a resistance heater.

8. The warmer of claim 7, wherein said resistance heater is in said enclosure so that said enclosure shields substantially all of said resistance heater.

9. The warmer of claim 7, further comprising a lighting device in said enclosure so that said enclosure shields substantially all of said lighting device.

10. The warmer of claim 9, wherein lighting device comprises a light emitting diode.

11. The warmer of claim 10, further comprising a decorative pattern defined on an external surface of said enclosure.

12. The warmer of claim 11, wherein said enclosure has a portion that is at least partially translucent.

13. The warmer of claim 1, wherein said warming device comprises a candle removably positionable on said base so that said cover shields substantially all of said candle with said candle being at a center of said opening.

14. The warmer of claim 13, further comprising at least one vent opening defined between said cover and said base.

15. The warmer of claim 14, wherein said least one vent opening comprises a plurality of evenly spaced indentations defined in said base.

16. The warmer of claim 13, further comprising a decorative pattern defined on an external surface of said cover.

17. The warmer of claim 13, wherein said cover is at least partially translucent.

18. The warmer of claim 1, further comprising a scented oil in a semi-solid form or a solid form pre-filled in said open channel.

* * * * *